United States Patent
Bjerke et al.

(10) Patent No.: US 7,721,947 B2
(45) Date of Patent: May 25, 2010

(54) BIOLOGICAL SAMPLE PROCESSING APPARATUS THAT SELECTS THE PERSONALITY TYPE OF THE APPARATUS

(75) Inventors: Michael P. Bjerke, Oregon, WI (US); Steven T. Krueger, Deerfield, WI (US); Louis Mezei, Fitchburg, WI (US)

(73) Assignee: Promega Corporation, Madison, WI (US)

( * ) Notice: Subject to any disclaimer, the term of this patent is extended or adjusted under 35 U.S.C. 154(b) by 209 days.

(21) Appl. No.: 11/763,915

(22) Filed: Jun. 15, 2007

(65) Prior Publication Data

US 2008/0010520 A1    Jan. 10, 2008

Related U.S. Application Data

(60) Provisional application No. 60/814,063, filed on Jun. 16, 2006.

(51) Int. Cl.
*G06F 17/00* (2006.01)
*G06K 7/10* (2006.01)
*G06K 7/00* (2006.01)
*G06K 19/06* (2006.01)

(52) U.S. Cl. .................. 235/375; 235/462.01; 235/486; 235/492

(58) Field of Classification Search .................. 235/375, 235/462.01, 486, 492; 702/31, 182, 183, 702/19, 22, 121, 123; 340/286.01
See application file for complete search history.

(56) References Cited

U.S. PATENT DOCUMENTS

| | | | |
|---|---|---|---|
| 4,873,633 A | 10/1989 | Mezei et al. .................. 356/39 |
| 5,742,683 A | 4/1998 | Lee et al. .................. 705/60 |
| 5,869,006 A * | 2/1999 | Fanning et al. .................. 422/67 |
| 5,891,396 A * | 4/1999 | Karl et al. .................. 422/65 |
| 6,086,824 A * | 7/2000 | Fanning et al. .................. 422/65 |
| 6,103,518 A * | 8/2000 | Leighton .................. 435/286.3 |
| 6,589,789 B1 | 7/2003 | Hubert et al. |
| 6,611,334 B1 | 8/2003 | Fernando et al. |
| 6,615,175 B1 | 9/2003 | Gazdzinski .................. 704/275 |
| 7,110,890 B2 * | 9/2006 | Birkett et al. .................. 702/31 |
| 2005/0089448 A1* | 4/2005 | Bishop et al. .................. 422/99 |
| 2005/0185217 A1 | 8/2005 | Nishizawa et al. .......... 358/1.15 |
| 2007/0010953 A1* | 1/2007 | Birkett et al. .................. 702/31 |

FOREIGN PATENT DOCUMENTS

WO    2007/149311    12/2007

OTHER PUBLICATIONS

International Search Report and Written Opinion for Application No. PCT/US2007/014029 dated May 22, 2008 (4 pages).

* cited by examiner

*Primary Examiner*—Thien M. Le
*Assistant Examiner*—April A Taylor
(74) *Attorney, Agent, or Firm*—Michael Best & Friedrich LLP

(57) ABSTRACT

A biological sample processing apparatus having a central processing unit, a display in communication with the central processing unit and a selector for selecting a personality type of the apparatus, the selector being in communication with the central processing apparatus. The selection of a personality type prompts the central processing unit to cause the display to show a list of preprogrammed protocols for biological sample processing that correspond to the selected personality type.

24 Claims, 3 Drawing Sheets

BIOLOGICAL SAMPLE PROCESSING APPARATUS THAT SELECTS THE PERSONALITY TYPE OF THE APPARATUS

This application claims the benefit of U.S. Provisional Patent Application No. 60/814,063, filed Jun. 16, 2006.

FIELD OF THE INVENTION

This invention relates to a biological sample processing apparatus having a selector for selecting a personality type of the apparatus. This invention provides a user of the apparatus with the ability to cull a list of preprogrammed protocols so that only those protocols of interest are shown. The culling of the preprogrammed list of protocols is performed by allowing the user to select between various personality types for the apparatus. For example, the user has the ability to designate the apparatus as a research apparatus, a clinical apparatus, or a forensic apparatus. Selection of the apparatus as a research apparatus, for example, would cause the display of the apparatus to show only the protocols of interest for research applications. The protocols that are applicable only to forensic applications and clinical applications would then be hidden. Selection of the apparatus as a forensic apparatus, for example, would cause the display of the apparatus to show only the protocols of interest for forensic applications. The protocols that are applicable only to research applications and clinical applications would then be hidden. And, selection of the apparatus as a clinical apparatus, for example, would cause the display of the apparatus to show only the protocols of interest for clinical applications. The protocols that are applicable only to research applications and forensic applications would then be hidden.

BACKGROUND OF THE INVENTION

Biological sample processing is an important technique, for example, for researchers and forensic scientists, and the processing of nucleic acids (e.g., DNA and RNA) and other biological material such as proteins has broad applications. Researchers can use processed nucleic acids to determine the genetic causes of diseases as well as to develop remedial therapies such as medicines and vaccines. Forensic scientists, for example, can use processed biological material to determine whether a suspect was the perpetrator of a crime.

The vast array of applications utilizing processed biological material has increased the demand by researchers and forensic scientists for apparatuses automating the protocols for processing (e.g., purifying) biological material. Automation is important for the consistency and reproducibility of biological processing protocols, as well as for chain of custody issues. For example, the ability to ensure that a processing protocol is performed accurately can help to alleviate questions and concerns about whether a particular sample was tainted or contaminated as a result of operator error. By having the ability to place a sample in an apparatus and let the apparatus processes the biological material in the sample without technician or researcher intervention can increase the credibility and reliability of the results of the processing run.

As a result of the demand for automation, a variety of corporations have created apparatuses capable of processing biological material. Some of these machines, such as the Freedom EVO® manufactured by Tecan Trading AG of Switzerland, the Biomek® 2000 Laboratory Automation Workstation, manufactured by Beckman Coulter of Fullerton, Calif., and the Eppendorf® epMotion™, manufactured by Eppendorf of Germany, have relatively high throughput capability. Others, such as the Maxwell™ 16 manufactured by Promega Corporation of Madison, Wis. have lower throughputs. Generally, the apparatuses that automate biological processing protocols are capable of storing a large number of protocols that can be selected by a user based on the particular protocol of interest. Additionally, many of these apparatuses will be used by corporations or institutions that perform basic research as well as forensic and clinical applications.

The potential for multiple setting usage (e.g., a research setting, a clinical setting, and a forensic science setting) of an apparatus increases the number of protocols that must be stored in the memory of the apparatus in order for the apparatus to satisfy the functionality demands of users. A variety of protocols, however, may only have single application functionality. That is, one protocol may be useful only in a basic research setting, whereas another protocol may be useful only in a forensic science setting or in a clinical setting. Despite having applicability in only one setting, each of the two protocols may be similar, or be named similarly, which can create confusion for a user. Any confusion can result in a user selecting the wrong protocol from a displayed list of all available protocols, resulting in error. To eliminate this potential source of confusion, there has been a demand for an apparatus that is capable of culling protocols based on, for example, whether the apparatus will be used only in a research setting or only in a forensic setting.

This invention is directed to satisfying this demand by providing an apparatus capable of having a designated personality. That is, the present invention is directed to a biological sample processing apparatus that allows a user to designate the personality of the apparatus. The personalities may include a forensic personality, a clinical personality, and a research personality, but are not limited thereto. The designation of a particular personality causes only the protocols associated with that personality to be displayed; all other protocols would remain hidden from the user.

SUMMARY OF THE INVENTION

In one aspect, the present invention is directed to a biological sample processing apparatus having a central processing unit, a display in communication with the central processing unit and means for selecting a personality type of the apparatus, the means for selecting being in communication with the central processing unit. The selection of a personality type prompts the central processing unit to cause the display to show a list of preprogrammed protocols for biological sample processing that correspond to the selected personality type.

Preferably, the personality types are a research personality, a clinical personality and a forensic personality.

The means for selecting a personality type include a user interface such as a keypad or a touch screen.

Additionally, the biological purification apparatus may further include an RFID reader, a barcode reader, a device capable of optical character recognition, and the means for selecting a personality type may include an RFID tag, a barcode, or word or phrase attached to a cartridge of wells configured for operable cooperation with the apparatus.

The apparatus may also include means for selecting a protocol mode such as a high volume mode or a low volume mode.

These and other aspects of the present invention will be apparent upon consideration of the following detailed description taken in conjunction with the accompanying drawings, in which preferred embodiments of the present invention are described and illustrated.

DESCRIPTION OF THE DRAWINGS

Throughout the figures, like or corresponding reference numerals denote like or corresponding parts.

DETAILED DESCRIPTION OF THE PRESENT INVENTION

The present invention relates to a biological sample processing apparatus including a selector for selecting a personality type of the apparatus. In this regard, an operator of the biological sample processing apparatus has the ability to cull the displayed protocols stored in a memory of the apparatus based on the selected personality type. By selecting a personality type for the apparatus, a user causes the apparatus to show only the protocols associated with that personality type. In addition to culling the list of available protocols to only those of interest to the user, the selection of a personality type of the biological sample processing apparatus also helps to eliminate mistakes that may occur from a user inadvertently selecting a protocol associated with another personality, especially in the case where two or more protocols for different personality types are similarly named. In this manner, the biological sample processing apparatus can be used to process DNA, RNA, proteins and other biological material of interest in a variety of settings (e.g., a research setting and a forensic science setting) repeatedly, reliably, and with less potential for error than with conventional biological sample processing apparatuses.

Additionally, the present invention is advantageous in that the selection of a personality type limits the number of menu choices, which increases the ease of use of the apparatus. Further, having the user select the personality type of the apparatus allows the manufacturer to ship the same software package with each apparatus, regardless of the setting in which the apparatus is used. That is, the same software package can be included in each apparatus, regardless of whether the apparatus is to be used in a research setting, a forensic science setting, or a clinical setting. This means that the manufacturer only has to maintain, inventory, and validate one software package, rather than numerous software packages tailored to particular settings.

Figure 1:
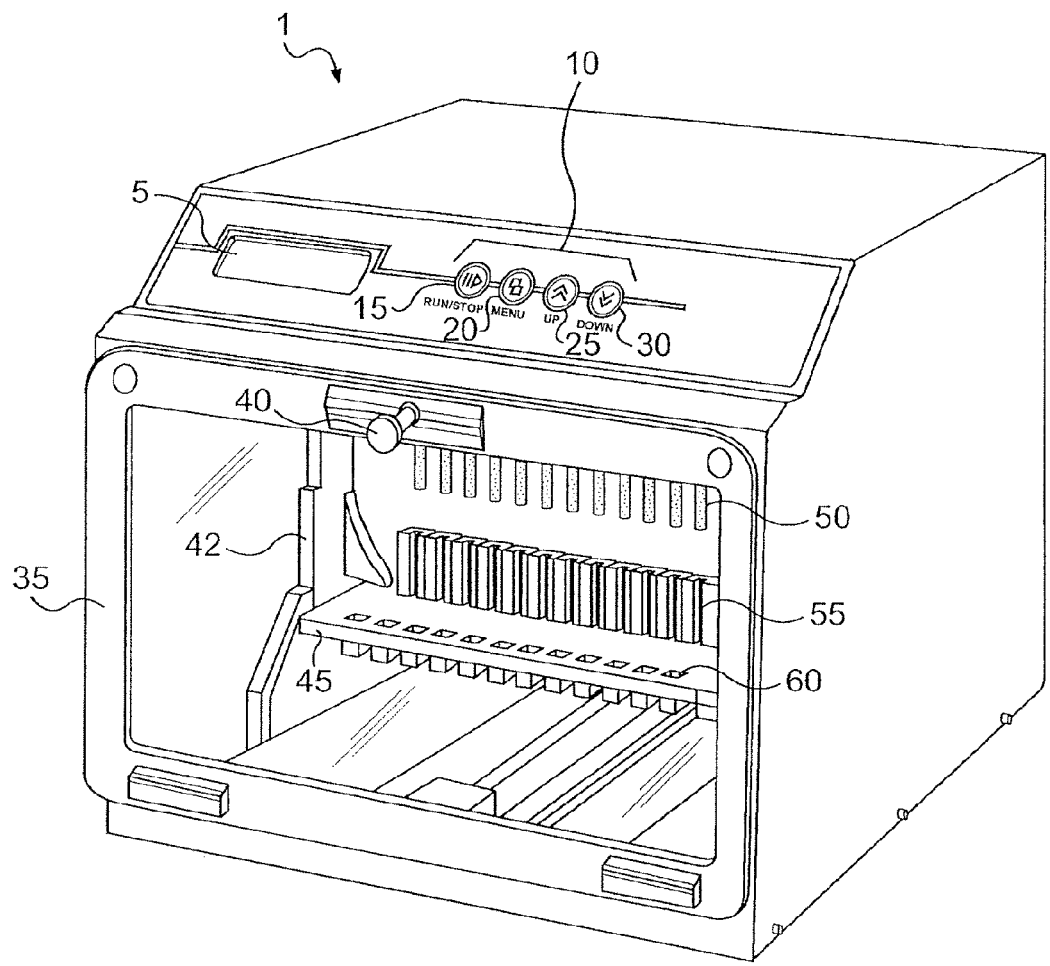
FIG. 1 is a perspective view of one embodiment of a biological sample processing apparatus according to the present invention.

FIG. 1 depicts one embodiment of the apparatus according to the present invention. The biological sample processing apparatus 1 has on its exterior a display screen 5 and keypad 10. In the embodiment depicted in FIG. 1, the keypad 10 has four keys, a RUN/STOP key 15, a MENU key 20, an UP key 25, and a DOWN key 30. It should be noted, of course, that biological sample processing apparatus 1 of the present invention is not limited to the display screen 5 and keypad 10. Other keypads, having more or fewer buttons, and other displays such as a touch-sensitive screen, for example, may be used in conjunction with or instead of the depicted display screen 5 and keypad 10.

In addition to the display screen 5 and keypad 10, the exterior of the biological sample processing apparatus 1 has a door 35 and a handle 40. By opening the door 35, a user gains access to the interior of the biological sample processing apparatus 1.

In the interior, the apparatus depicted in FIG. 1 has a frame 42. Connected to the frame 42 is a platform 45, which is movable along the dimension of depth; that is, the platform 45 may move toward and away from the door 35. Also connected to the frame 42 are plunger rods 50. The plunger rods are movable in a direction of height. In FIG. 1, the plunger rods 50 are in an upper position. During operation of the apparatus, the plunger rods 50 may descend toward platform 45. Further, at the rear of platform 45 are reagent cartridge slots 55. In a reagent cartridge slot 55, the user may place a cartridge 65, shown in FIG. 2. Additionally, the biological sample processing apparatus 1 may include heated elution tube slots 60.

The biological sample processing apparatus 1 further includes a central processing unit (not shown) that is in communication with the display screen 5 and keypad 10. A non-volatile memory such as an EEPROM stores a number of protocols for biological purification. Based on the protocol selection by a user, the central processing unit accesses the non-volatile memory for the desired protocol and controls the movement of the platform 45 and the plunger rods 50, and depending on the protocol, the heating of the heated elution tube slots 60.

Figure 2:
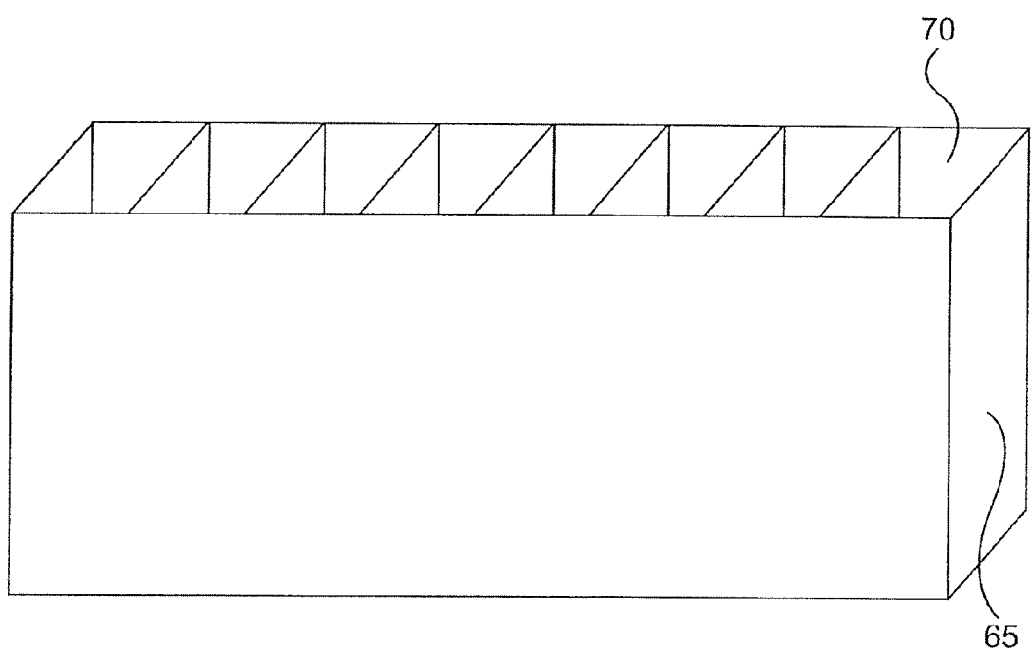
FIG. 2 depicts of a cartridge having wells for use with the biological sample processing apparatus.

FIG. 2 depicts a cartridge 65 that may be used with the apparatus depicted in FIG. 1. The cartridge 65 has wells 70 into which various chemicals and solutions, such as a lysis solution or a wash solution, may be placed. The cartridges may be pre-filled by the manufacturer or may be filled by a researcher or technician based on the particular biological sample processing application or protocol of interest. Each well 70 in the cartridge 65 corresponds to a step in a biological sample processing process. One end (not shown) of the cartridge 65 is adapted to fit in a reagent cartridge slot 55.

In general terms, the apparatus operates by first having the user/operator place a cartridge 65 in a reagent cartridge slot 55 on platform 45 and any necessary elution tubes in heated elution tube slots 60. Then, after a protocol has been selected, the plunger rods 50 descend into the wells 70 of the cartridge 65. The biological material of interest is attracted to the plunger rods 50 by magnetic force or another method, such as a chemical reaction. As the platform 45 moves from a first position to an end position, the platform 45 stops at positions corresponding to the location of each well 70 of cartridge 65. Once in position, the plunger rods 50 descend into the wells 70 and remain in that position for a predetermined period of time. Of course, it is possible that at a particular well location the plunger rods will descend into and ascend from that well repeatedly, depending on the particulars of the selected protocol. Once the predetermined period of time has elapsed, the plunger rods 50 ascend, and the platform 45 moves to a position corresponding to the location of the next well 70. The plunger rods 50 again descend and stay in that position for a predetermined period of time. This process is repeated until the platform 45 reaches a position whereby the plunger rods 50 are positioned directly above the heated elution tube slots 60. In a one-pass protocol, once the plunger rods 50 descend into and ascend from the heated elution tubes, the processing protocol is complete and the user can remove the cartridge 65 from the platform 45. In a multi-pass protocol, once the plunger rods have descended into and ascended from the heated elution tubes, the platform returns to an earlier position and another pass is performed from that position. This process continues until the indicated number of passes have been completed.

The movement of the plunger rods 50 into each well 70 of cartridge 65 allows for the processing of a target biological material. For example, as a first step, the plunger rods 50 descend into a well containing a sample containing the target biological material, a lysis solution, and magnetic particle solution. The lysis solution lyses the cells of the sample, and the biological material of interest complexes with the magnetic particles. The plunger rods 50, which may be magnetized, descend into the well and extract the biological material of interest based on a magnetic attraction between the plunger rods and the biological material—magnetic particle complex. The plunger rods then ascend from the well, the platform moves to the next location, which corresponds to the location of the next well. This well may have, for example, a wash solution. The plunger rods descend into the well and the extracted biological material is washed. The plunger rods ascend from the well, and the process of descending into and ascending from the wells of the cartridge continues according to the strictures of the biological sample processing protocol. Finally, the processed biological material may be eluted in the heated elution tubes placed in heated elution tube slots 60. At this point, the user may recover the processed biological material.

Figure 3:
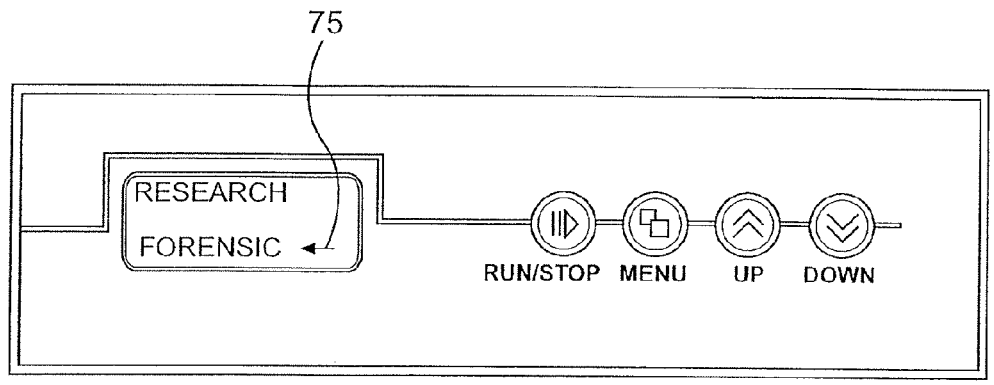
FIG. 3 depicts of the display showing the available personality types of a biological sample processing apparatus according to the present invention.

Prior to first using the biological sample processing apparatus, however, the user selects the desired personality. To select the personality, the user plugs in and turns on the biological sample processing apparatus. After initial setup functions have been performed, the display screen 5 displays the available personality types. As shown in FIG. 3, the user may select between personality types such as a RESEARCH personality or a FORENSIC personality, for example. Of course, other personality types, such as a clinical personality, may be shown in addition to or instead of the research and forensic personalities. To select the desired personality, the user presses UP key 25 or DOWN key 30 to toggle between available personality types. When cursor 75 is adjacent to the desired personality type, the user presses RUN/STOP key 15.

After the user selects the personality, the display may prompt the user for verification of selected identity. This verification step helps prevent a user from inadvertently selecting the wrong personality, especially since with the personality selection the biological sample processing apparatus assumes that personality and maintains that personality without further prompting from the user. That is, once the apparatus has been designated as having a RESEARCH personality, the apparatus will always have a RESEARCH personality, and there is no need for a user to select the personality of the apparatus prior to each run. The data indicating the selected personality type may be stored in the non-volatile memory.

If the user desires to change the selected personality, the user would need to access the initial setup functions of the biological sample processing apparatus to deselect and reselect a personality type. The fact that the biological sample processing apparatus maintains the selected personality type is advantageous because it mitigates user error and instills confidence that the biological sample processing apparatus will perform only the desired protocol(s). An institution or laboratory would not need to worry that a new or harried user will inadvertently select an inappropriate personality, which could thereby taint, contaminate or even destroy a particular biological sample.

Figure 4:
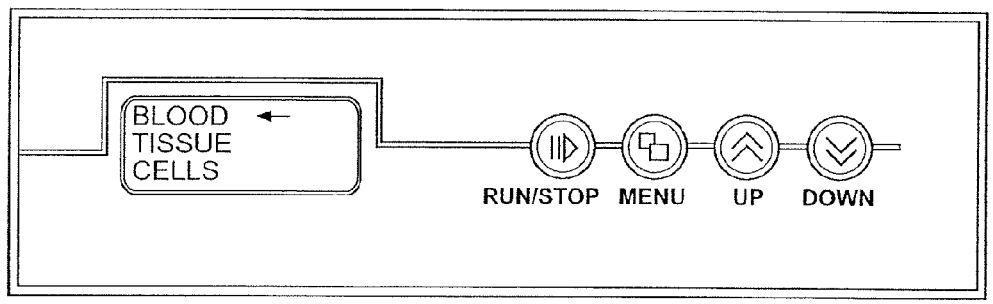
FIG. 4 depicts of the display showing available protocols once a personality has been selected.

Once the personality type has been selected, the display shows a list of all protocols associated with that personality type. For example, as shown in FIG. 4, the user may choose between a BLOOD protocol, a CELLS protocol and a TISSUE protocol. To select the desired protocol, the user again toggles between the displayed protocols by pressing either the UP key 25 or the DOWN key 30. When the cursor 75 is adjacent to the desired protocol, the user presses RUN/STOP key 15. It should be noted that there may be additional or fewer display screens depending on the number of protocols stored in the non-volatile memory and the manner in which the selection process is broken down. For instance, if the biological sample processing apparatus stores protocols for processing genomic DNA, RNA and proteins from cells, tissue and blood, the first display screen following the personality selection verification screen may prompt the user to select between DNA, RNA and PROTEINS. Following this selection, the user may then select from between CELLS, TISSUE and BLOOD. Alternatively, the protocols may be grouped together so that the user selects from, for example, DNA BLOOD, RNA BLOOD, PROTEIN BLOOD, etc. Or, in another alternative, the selection may be limited simply to selection between CELLS, TISSUE, and BLOOD. Of course, the invention is not limited to the above-described methods of selecting the desired protocol, and other methodologies are included within the scope of this invention.

Depending on the sophistication of the apparatus, once the user selects BLOOD, TISSUE, or CELLS, the display screen may prompt the user for verification that the selected protocol is the desired protocol. If the user verifies that the selected protocol is the desired protocol, the apparatus will begin to perform the selected protocol.

If the user mistakenly selected the protocol, the user would indicate on the verification screen that a mistake was made and the display would return to the protocol selection screen at which point the user would have the ability to select the desired protocol. Alternatively, if at any point during the protocol selection process, the user realizes that an error has been made, the user may press the MENU key 20 to return to the beginning of the protocol selection process.

Figure 5:
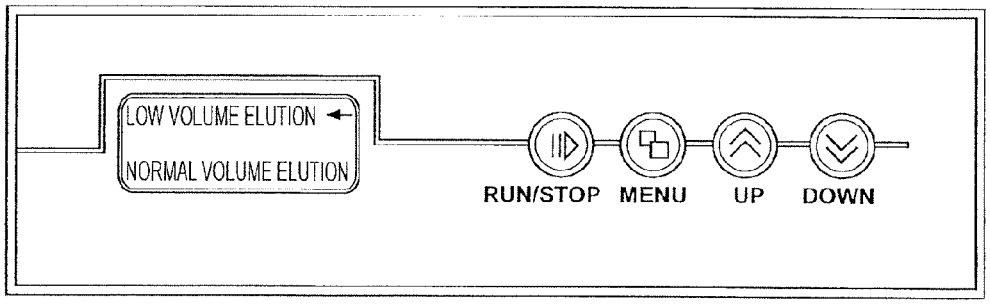
FIG. 5 depicts of the display showing available protocol modes.

Additionally, the apparatus may have functionality such that, once the user selects the desired protocol, the user may be prompted, as shown in FIG. 5, to select whether the desired protocol is to be run as a NORMAL VOLUME ELUTION protocol mode, or as a LOW VOLUME ELUTION protocol mode, for example. The selection of the elution volume mode controls the distance the plunger rods descend during operation. It should be noted that the LOW VOLUME/NORMAL VOLUME elution mode selection alternatively may be incorporated into the personality selection. That is, initially, the user may select from HIGH VOLUME RESEARCH, LOW VOLUME RESEARCH, HIGH VOLUME FORENSIC, and LOW VOLUME FORENSIC personalities, or other such combinations of mode and personality type.

In addition to the volume selection, the user may also be prompted to select the number of plunger rods that are needed, the number of passes to be performed during the protocol, and the temperature to which the elution tubes are to be heated, etc. Once all selections have been made and the user has verified that the selections are correct, the apparatus performs the selected biological sample processing protocol.

In an alternative to the embodiment in which the user selects the personality of the apparatus via the display screen 5 and the keypad 10, the personality selection, protocol selection, and mode selection may instead be based on a radio frequency identification (RFID) tag affixed to cartridge 65. According to this embodiment, the apparatus would include a reader (not shown) capable of reading RFID tags (not shown). When the user wants to run a particular protocol, the user would select either the appropriate RFID tag and affix it to a cartridge 65, or the user would select a cartridge 65 already having an affixed RFID tag affixed thereto. The user would then open the door 30, place the cartridge 65 on the platform 45 and close the door. Once the door is closed, the reader would scan the interior of the biological sample processing apparatus and read the RFID tag on the cartridge. Once the RFID tag is read, the biological sample processing apparatus would run the indicated protocol.

In another alternative, the apparatus would include a barcode reader (not shown) to read a barcode affixed to a cartridge 65. When the user wants to run a particular protocol, the user would select either the appropriate barcode and affix it to a cartridge 65, or the user would select a cartridge already having a barcode affixed thereto. The user would then open the door 30, place the cartridge 65 on the platform 45 and close the door. Once the door is closed, the barcode reader would scan the interior of the biological sample processing apparatus and read the barcode on the cartridge. Once the barcode is read, the biological sample processing apparatus would run the indicated protocol.

In yet another alternative, the apparatus would include a device capable of optical character recognition (OCR). To run a particular protocol, a user would either affix a word or phrase to a cartridge 65 or select a cartridge having a word or phrase corresponding to the particular protocol of interest affixed thereto. The user would then open the door 30, place the cartridge 65 on the platform 45 and close the door. Once the door is closed, the device would then scan the interior of the apparatus and read the word or phrase on the cartridge. Once the word or phrase is read, the biological sample processing apparatus would run the indicated protocol.

Use of an RFID tag, a barcode, or OCR system could further prevent user error by limiting opportunities for the user to make an error. If to run a particular protocol the user merely has to choose, for example, the appropriate RFID tag, or cartridge containing an RFID tag, rather than selecting various options by toggling between choices shown on the display screen 5, the potential sources of error are limited, further increasing the reliability of the biological sample processing procotol.

While the present invention has been described with reference to explanatory embodiments, it is to be understood that the terms used herein are terms of description rather than limitation. Various changes and modifications may be made without departing from the scope and spirit of the present invention as set forth in the appended claims.

We claim:

1. A biological sample processing apparatus comprising:
a central processing unit;
a display in communication with the central processing unit; and
means for selecting a personality type of the apparatus, the means for selecting being in communication with the central processing unit,
wherein selection of a personality type prompts the central processing unit to cause the display to show a list of preprogrammed protocols for biological sample processing that correspond to the selected personality type, and
wherein the apparatus comprises one of:
  (a) an RFID reader, and the means for selection is an RFID tag attached to a cartridge of wells configured for operable cooperation with the apparatus;
  (b) a barcode reader, and the means for selection is a barcode attached to a cartridge of wells configured for operable cooperation with the apparatus; or
  (c) a device capable of optical character recognition, and the means for selection is a word or phrase attached to a cartridge of wells configured for operable cooperation with apparatus.

2. The apparatus according to claim 1, wherein the apparatus further includes a non-volatile memory in communication with the central processing unit, and wherein data indicating a selected personality type is stored in the non-volatile memory.

3. The apparatus according to claim 1, further comprising means for selecting a protocol mode.

4. The apparatus according to claim 1, further comprising means for selecting between a normal volume elution mode and a low volume elution mode.

5. The apparatus according to claim 1, wherein the personality type is a research personality, a clinical personality, or a forensic personality.

6. A biological sample processing apparatus comprising:
a frame having a depth dimension, a width dimension and a height dimension;
at least one plunger slidably mounted to the frame;
a platform slidably mounted to the frame, the platform being positioned below the at least one plunger;
a central processing unit connected to the frame;
a display in communication with the central processing unit; and
means for selecting a personality type of the apparatus, the means for selecting being in communication with the central processing unit,
wherein the plunger is slidable in the height dimension,
wherein the platform is slidable in the depth dimension,
wherein selection of a personality type prompts the central processing unit to cause the display to show a list of preprogrammed protocols for biological sample processing that correspond to the selected personality type, and
wherein when a user selects a protocol from the list of preprogrammed protocols, the central processing unit controls movement of the at least one plunger and the platform.

7. The apparatus according to claim 6, wherein the means for selection is a user interface.

8. The apparatus according to claim 7, wherein the user interface is a keypad or a touch screen.

9. The apparatus according to claim 6, wherein the apparatus further comprises an RFID reader, and the means for selection is an RFID tag attached to a cartridge of wells configured for operable cooperation with the apparatus.

10. The apparatus according to claim 6, wherein the apparatus further includes a barcode reader, and the means for selection is a barcode attached to a cartridge of wells configured for operable cooperation with the apparatus.

11. The apparatus according to claim 6, wherein the apparatus further includes a device capable of optical character recognition, and the means for selection is a word or phrase attached to a cartridge of wells configured for operable cooperation with apparatus.

12. The apparatus according to claim 6, wherein the apparatus further includes a non-volatile memory in communication with the central processing unit, and wherein data indicating a selected personality type is stored in the non-volatile memory.

13. The apparatus according to claim 6, further comprising means for selecting a protocol mode.

14. The apparatus according to claim 6, further comprising means for selecting between a normal volume elution mode and a low volume elution mode.

15. The apparatus according to claim 6, wherein the personality type is a research personality, a clinical personality, or a forensic personality.

16. A biological sample processing apparatus comprising:
   a central processing unit;
   a display in communication with the central processing unit;
   a personality type selector, the personality type selector being in communication with the central processing unit; and
   means for selecting between a normal volume elution mode and a low volume elution mode,
   wherein selection of a personality type with the personality type selector prompts the central processing unit to cause the display to show a list of preprogrammed protocols for biological sample processing that correspond to the selected personality type.

17. The apparatus according to claim 16, wherein the personality type selector is a user interface.

18. The apparatus according to claim 17, wherein the user interface is a keypad or a touch screen.

19. The apparatus according to claim 16, wherein the apparatus further comprises an RFID reader, and the personality type selector is an RFID tag attached to a cartridge of wells configured for operable cooperation with the apparatus.

20. The apparatus according to claim 16, wherein the apparatus further includes a barcode reader, and the personality type selector is a barcode attached to a cartridge of wells configured for operable cooperation with the apparatus.

21. The apparatus according to claim 16, wherein the apparatus further includes a device capable of optical character recognition, and the personality type selector is a word or phrase attached to a cartridge of wells configured for operable cooperation with apparatus.

22. The apparatus according to claim 16, wherein the apparatus further includes a non-volatile memory in communication with the central processing unit, and wherein data indicating a selected personality type is stored in the non-volatile memory.

23. The apparatus according to claim 16, further comprising means for selecting a protocol mode.

24. The apparatus according to claim 16, wherein the personality type is a research personality, a clinical personality, or a forensic personality.

* * * * *